United States Patent [19]
Lauro

[11] Patent Number: 6,154,678
[45] Date of Patent: Nov. 28, 2000

[54] STIMULATION LEAD CONNECTOR

[75] Inventor: B. Reno Lauro, Murphy, Tex.

[73] Assignee: Advanced Neuromodulation Systems, Inc., Allen, Tex.

[21] Appl. No.: 09/272,847

[22] Filed: Mar. 19, 1999

[51] Int. Cl.[7] .................................................. A61N 1/04
[52] U.S. Cl. ............................................................ 607/115
[58] Field of Search ................................. 607/115, 119, 607/37, 38, 116, 122; 439/909; 600/373–381

[56] References Cited

U.S. PATENT DOCUMENTS

| | | | |
|---|---|---|---|
| 4,850,359 | 7/1989 | Putz | 128/642 |
| 5,082,453 | 1/1992 | Stutz, Jr. | 439/265 |
| 5,241,957 | 9/1993 | Camps et al. | 607/119 |
| 5,348,481 | 9/1994 | Oriz | 439/25 |
| 5,354,326 | 10/1994 | Comben et al. | 607/115 |
| 6,038,479 | 3/2000 | Werner et al. | 607/115 |

Primary Examiner—Jeffrey R. Jastrzab
Attorney, Agent, or Firm—Sidley & Austin

[57] ABSTRACT

A stimulation lead connection assembly capable of easily receiving and engaging a stimulation lead for purposes of transmitting selected electrical energy to electrodes of a received stimulation lead. The connection assembly retains a stimulation lead in a manner that permits a user to freely insert (and/or withdraw) a steering mechanism, for example, a stylet, into the stimulation lead that is electrically engaged by the connection assembly.

9 Claims, 3 Drawing Sheets

STIMULATION LEAD CONNECTOR

FIELD OF THE INVENTION

The present invention relates to a stimulation lead connector, and in particular, to a stimulation lead connector capable of readily engaging a stimulation lead and/or enabling the stimulation lead to be freely controlled using a stylet or other like steering mechanism during engagement.

BACKGROUND OF THE INVENTION

For medical applications, administering particularized electrical energy to prescribed regions of the human body can achieve symptomatolytic effects for a variety of conditions, including chronic pain and certain motor disorders, or restore cardiac rhythms in heart tissue subject to fibrillation. Whether a stimulation lead is positioned in the brain, in the heart, along a peripheral nerve, or in the epidural space of a dorsal column, the positioning of the stimulation lead is critical to the effectiveness of subsequently delivered stimulation and prevention of undesirable, extraneous stimulation. Consequently, positioning a stimulation lead typically represents the most time intensive aspect of a stimulation lead implantation procedure.

To briefly describe a typical stimulation lead implantation procedure, a user first places a stimulation lead, whether through surgical intervention or otherwise, in the general region to be stimulated. Electrical energy is delivered through the stimulation lead, and a user guides the stimulation lead to a final placement position based on patient and/or physiological feedback. During this placement exercise, the stimulation lead is typically coupled to an electrical energy source, for example, an electrical pulse generator, through a temporary connector.

Conventional temporary connectors, at least in the field of spinal cord stimulation, are unfortunately not convenient to use. One such form of connector is the set screw-type connector.

Set screw connectors consist generally of a sleeve defining a longitudinal passage that receives the connector portion of a stimulation lead. The set screw connector has a plurality of "contacts" positioned along the length of the sleeve, each contact being formed of a removable set screw. The set screws span between an exterior surface of the sleeve and an interior surface of the sleeve and are adjustable so as to extend into, or retract from, the longitudinal passage.

Conventional stimulation leads can include four or more electrodes. As the set screws are quite small, understandably a user must be vigilant in initially loosening the set screws (i.e., to open the longitudinal passage of the connector) not allow a set screw to become free of the connector. Once a stimulation lead is positioned within the longitudinal passage, each set screw must be properly tightened to ensure contact with each contact of a received stimulation lead. Unless a torque wrench is used, care must be taken to limit the amount of force applied to each set screw to prevent damage to a received stimulation lead.

Some stimulation leads may include additional structure to aid in their steerability during placement. For stimulation leads that are introduced into a patient through a needle, for example, the stimulation lead may include an internalized stiffening wire to enhance the rigidity of the stimulation lead. As a further alternative, a stimulation lead may include a centralized passage to receive a steering mechanism, for example, a flexible stylet. The centralized passage opens at or near the proximal end of the stimulation lead to receive the flexible portion of a steering mechanism. Manipulation of the steering mechanism, as opposed to the stimulation lead or the connector, prevent inadvertent physical damage to the stimulation lead and/or connector.

In addition to the burden associated with tightening and loosening a plurality of set screws to engage/release a stimulation lead, known set screw-type connectors do not allow use of a flexible stylet when operatively engaged. Consequently, when positioning a stimulation lead having a stylet, a user is forced to either disregard the stylet or repeatedly connecting/disconnecting the stimulation lead between steps of positioning and applying electrical energy. In regard to the latter option, such task can be overwhelming when each connection/disconnection may require the management of a significant number of set screws.

Other connectors, for example, a cylindrical twist connector manufactured by Medtronic, Inc. for use with at least its Pisces® Quad stimulation leads, alleviate some of the burden in quickly establishing an electrical connection between the connector and the stimulation lead. Similar to the set screw-type connectors described above, however, the twist-type connectors also do not allow use of a flexible stylet when the stimulation lead is operatively engaged.

Accordingly, a first need exists for a connector that easily and quickly engages/releases at least a connector portion of a stimulation lead. A second need exists, whether in conjunction with such first need or otherwise, for a connector that provides access to a steering mechanism inlet of a stimulation lead when the connector engages the stimulation lead.

SUMMARY OF THE INVENTION

One aspect of the present invention is directed to a connector to receive at least a portion of a stimulation lead adapted to accept a steering mechanism through a steering mechanism inlet. The connector includes a housing and at least one contact to electrically engage a contact portion of a stimulation lead received within a receiving portion of the housing. The housing is adapted to provide access to a steering mechanism inlet of a received, engaged stimulation lead to enable selective insertion or withdrawal of a steering mechanism through such steering mechanism inlet.

Another aspect of the present invention is directed to a connector to receive at least a portion of a stimulation lead adapted to accept a steering mechanism through a steering mechanism inlet. The connector includes a housing and at least one contact to electrically engage a contact portion of a stimulation lead received within a receiving portion of the housing. The at least one contact is selectively movable from at least a first position to a second position, wherein the at least one contact electrically engages the contact portion of a stimulation lead when the at least one contact is at the second position. The housing is adapted to provide access to a steering mechanism inlet of an engaged stimulation lead to enable selective insertion or withdrawal of a steering mechanism through such steering mechanism inlet.

Another aspect of the present in directed to a connector to receive at least a portion of a stimulation lead. The connector includes a housing, at least one contact, movable from at least a first position to a second position, to electrically engage a stimulation lead received within a receiving portion of the housing, and an actuator to effect a translation of the at least one contact from the first position to the second position. The at least one contact electrically engages a received stimulation lead when such contact(s) is in the second position.

An object of the present invention is to provide a connector having a configuration that enables a user to quickly and easily engage/disengage at least a connector portion of a stimulation lead.

Another object of the present invention, whether in conjunction with other objects or otherwise, is to provide a connector having a configuration which provides access to a steering mechanism inlet of a stimulation lead when the stimulation lead is engaged by the connector.

Other objects and advantages of the present invention will be apparent to those of ordinary skill in the art having reference to the following Specification together with the provided drawings.

BRIEF DESCRIPTION OF THE DRAWINGS

In reference to the following figures, like reference numerals and letters indicate corresponding elements.

DETAILED DESCRIPTION OF THE PREFERRED EMBODIMENTS

Various embodiments, including preferred embodiments, will now be described in detail below with reference to the drawings.

Figure 1:
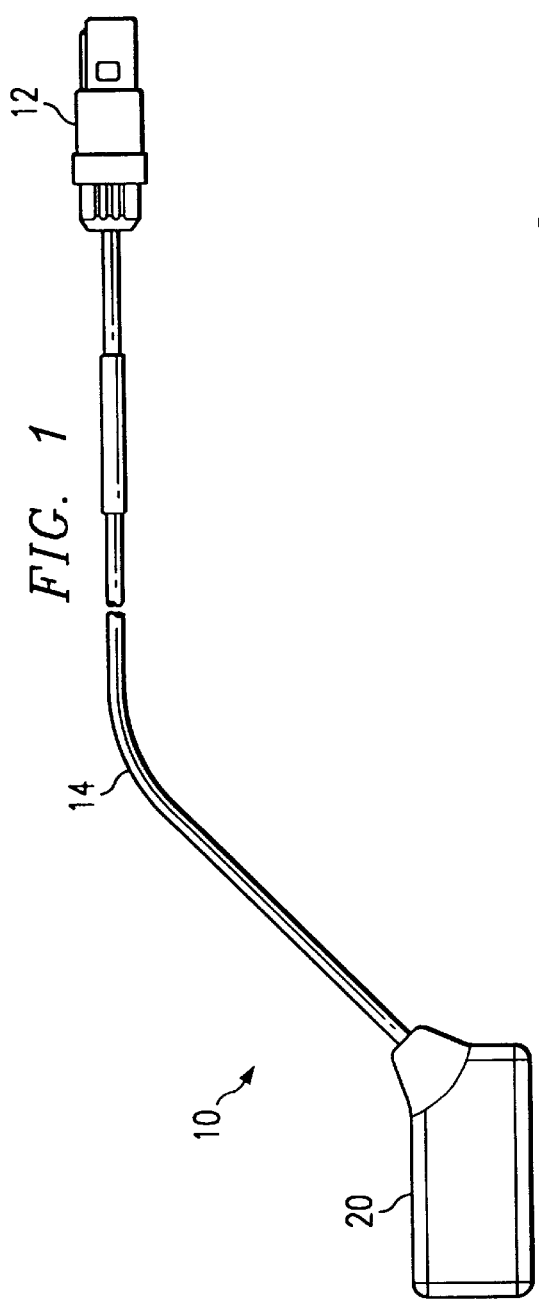
FIG. 1 illustrates one embodiment of a connection assembly in accordance with the present invention.

FIG. 1 illustrates one embodiment of connection assembly 10. Connection assembly 10 includes housing 20, connector 12, and cable 14 extending therebetween. The configuration of connector 12 is dictated by a selected electrical energy source (not shown), for example, a direct circuit source, an electrical pulse generator, or the like, used to generate electrical energy for transmission to an engaged stimulation lead (not shown).

Figure 2:
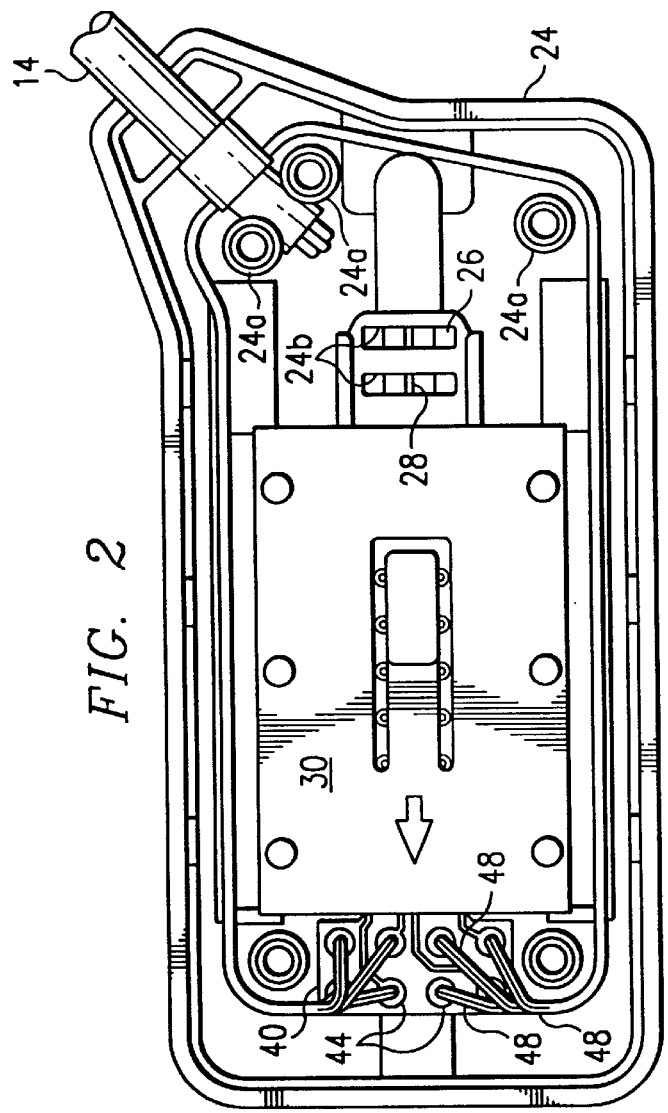
FIG. 2 is a sectional view of the connection assembly of FIG. 1 taken along line II—II of FIG. 1.
Figure 3:
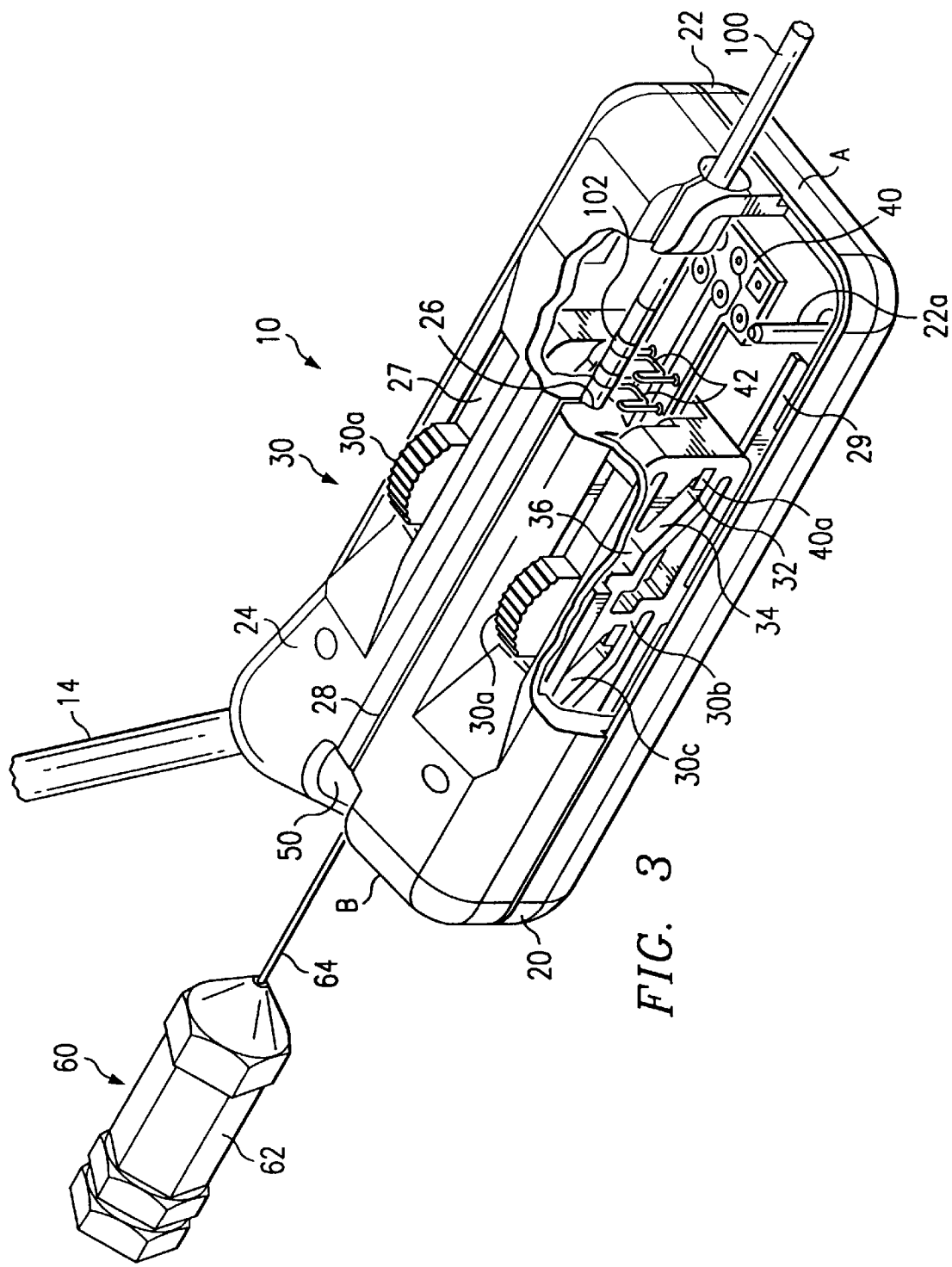
FIG. 3 is a partially sectional, perspective view of the connection assembly of FIG. 1, shown in a disengaged position.
Figure 4:
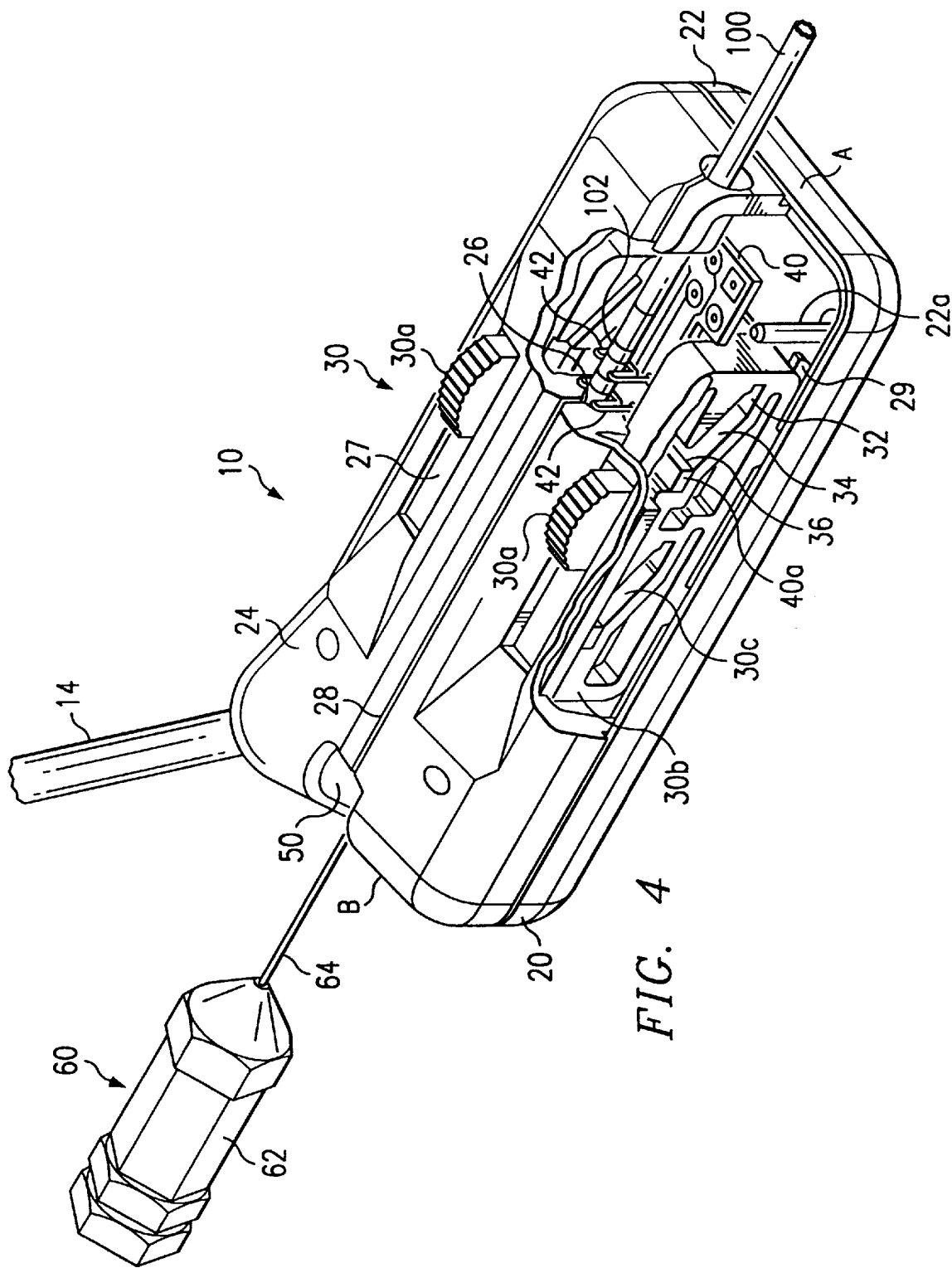
FIG. 4 is a partially sectional, perspective view of the connection assembly of FIG. 1, shown in an engaged position.

In reference to FIGS. 2–4, housing 20 is formed of lower housing 22 and upper housing 24. Lower housing 22 and upper housing 24 may be fixed together using an adhesive, weld, or the like, or press-fit together using, for example, one or more receptacles 24a, formed on an interior surface of upper housing 24, that receives tight-fitting members 22a.

In a preferred embodiment, upper housing 24 includes an internalized passage 26 to receive connector portion 102 of stimulation lead 100. Passage 26 has a substantially constant cross-section for a significant portion of its length relative to housing 20. At a distal portion 28 of passage 26, however, the cross-section of passage 26 preferably narrows to facilitate self-positioning of a received stimulation lead 100.

Passage 26 is accessible overhead through opening 28. While opening 28 preferably extends from a distal face (A) to a proximal face (B) of housing 20, opening 28 may extend for only a portion of housing 20.

As described in greater detail in the background section of this disclosure, some stimulation leads may include or accommodate additional structure to aid in the placement thereof. Steerable stimulation leads typically include a channel extending for some length along a longitudinal axis of the stimulation lead. The channel can include a permanently positioned stiffening wire or, alternatively, the passage may open at or near the proximal end of the stimulation lead (hereinafter "a steering mechanism inlet") to receive a flexible wire of a stylet or like controller.

Opening 28 allows passage of a stimulation lead steering mechanism, for example, stylet 60 having handle 62 and flexible wire 64. In a preferred embodiment, passage 26 is formed to guide flexible wire 64 to a steering mechanism inlet (not shown) of a received stimulation lead (e.g., stimulation lead 100). Thus, passage 26 and opening 28 cooperate to allow a user to first position stimulation lead 100 within passage 26 and then insert stylet 60. Alternatively, depending upon the configuration of opening 28 (see FIGS. 3 and 4), stimulation lead 100, already having stylet 60 positioned therein, may be positioned within passage 26.

Upper housing 24 of housing 20 accommodates at a least a portion of actuator 30 through openings 27. Actuator 30 comprises a user-accessible portion 30a, which allows a user to select an engagement/disengagement of stimulation lead 100 positioned within passage 26, and portion 30b, which effects the instruction of the user. Specifically, portion 30b, which will be discussed in greater detail below, effects the movement of contacts 42 from a disengaged position to an engaged position, or vice versa. While various guides and stops may be used to limit a range of motion of actuator 30, in a preferred embodiment, openings 27 and guides 29 limit the longitudinal and/or the transverse motion of actuator 30.

In a preferred embodiment, substrate 40, for example, a printed wiring board, carries at least one contact 42 and is preferably formed to have at least one extension 40a that transversely extends from a main body of substrate 40. In a most preferred form, substrate 40 includes four extensions 40a, wherein two extensions 40a are located along each longitudinal side of substrate 40.

While contacts 42 may assume any configuration or comprise any structure which readily enables engagement and disengagement of connector portion 102 (e.g., pad contacts, sleeve contacts, brushes, wire contacts, and the like), in the illustration of FIGS. 3 and 4, contacts 42 are wire and are formed generally in the shape of a "U". As shown in FIG. 4, when stimulation lead 100 is engaged, contacts of the received connector portion 102 rests within the "U" form of contacts 42.

In considering the form of contacts 42, it should be noted that contacts 42 may not only be used to establish an electrical connection with stimulation lead 100 but also to physically retain stimulation lead 100 within passage 26 when connection assembly 10 is in an engaged state. In addition, or as an alternative approach, substrate 40 may be provided with an element (not shown) to press against stimulation lead 100 and inhibit its removal from passage 26 when connection assembly 10 is in an engaged state.

In a preferred embodiment, connection assembly 10 has at least one pair of contacts 42. In a most preferred embodiment, connector assembly 10 has two, four, six, eight, ten, twelve, fourteen, sixteen, or twenty contacts 42. Each contact 42 is connected to a corresponding point 44 (FIG. 2). Operatively, electrical signals are selectively supplied to points 44 through conductors 48 (FIG. 2), wherein conductors 48 extend to connector 12 (FIG. 1).

To clarify the functionality of connection assembly 10, actuator 30 includes driving slot(s) 30c that receives extension 40a of substrate 40. Driving slots 30c include first landing 32, second landing 36, and transition 34 that joins landings 32 and 36. In a preferred embodiment, landings 32 and 36 each have a dimension sufficient to support extension 40a.

As may be seen in FIGS. 3 and 4, landing 34 is vertically displaced from landing 32, and such vertical displacement facilitates the vertical translation of substrate 40 upon movement of actuator 30. The range of vertical displacement is a function of at least passage 26, contacts 42, and the dimensions of connector portion 102 of stimulation lead 100, wherein it is important to establish a complete and reliable electrical connection between contacts 42 and stimulation lead 100 while avoiding damage to either contacts 42 or stimulation lead 100 through full vertical displacement of substrate 40.

In reference to FIG. 3, connector assembly 10 is shown in a disengaged state, i.e., extensions 40a are positioned on landings 32. In FIG. 4, connector is shown in an engaged state, i.e., extensions 40a having traveled along transitions 34, via actuation of portions 30a, to rest at landings 36. Consequently, movement of substrate 40 from landing 32 to landing 36 results in contact between contacts 42 and connector portion 102 of stimulation lead 100. Contacts 42 access stimulation lead 100 through openings 24b (FIG. 2) formed in that portion of upper housing 24 that defines passage 26. In the illustrated embodiments, openings 24b are perpendicular to a longitudinal direction of passage 26 and are aligned so as to receive contacts 42. Openings 24b have no required form; however, openings 24b should accommodate the selected configuration of contact 42 while also leaving sufficient material to form passage 26 to guide a received stimulation leads during its insertion.

In a preferred embodiment, the proximal face (B) of upper housing 24 is formed to include ramp 50 at the proximal end of opening 28. Ramp 50 engages a forward face of handle 62 of stylet 60. Operatively, if actuator 30 were moved to a disengaged position and stimulation lead 100 was freely removable from connection assembly 10, drawing stimulation lead 100 from connection assembly 10 should not effect an inadvertent withdrawal of stylet 60 from stimulation lead 100. To this end, ramp 50 prevents handle 62 from being fixed against housing 20 during extraction of stimulation lead 100.

The arrangement of contacts 42 and the cross-sectional area of passage 26 are dictated by the configuration of the connector portion of a stimulation lead. While the illustrated connector assembly 10 of the present invention is directed to receiving a stimulation lead having a generally circular cross-section with a plurality of in-line contacts, it should be readily appreciated that passage 26 may assume substantially any cross-sectional geometry to accommodate a connector portion of a stimulation lead. Likewise, contacts 42 may be arranged in any pattern to engage one or more contacts, having a corresponding pattern, of a received connector portion of a stimulation lead.

While the description set forth above is directed to an embodiment illustrated in FIGS. 2–4, it should be appreciated that substrate 40 could have any number of extensions 40a, including only one, wherein an appropriate number of slots 30c would be provided to accommodate such extensions 40a. Of note, the illustrated embodiment of FIGS. 3 and 4, which have four extensions 40a, provides equalized support with respect to substrate 40 to allow continuous transition from disengagement to engagement, and vice versa, as well as facilitate a distribution of applied force to effect engagement and disengagement.

Although actuator 30 has been illustrated and described in a specific form, it should be appreciated that actuator 30 could assume a number of differing structures to effect the translation of contacts 42 from an engaged state to a disengaged state (and vice versa). Examples of such forms, include but are not limited to: a user-accessible rotational member fixed to either a rotatable inclined plane supporting substrate 40 or a cam supporting substrate 40, wherein rotation of the rotational member effects a vertical translation of substrate 40; a user-accessible lever member to selectively move substrate 40 in a direction opposite to that of a force applied to the lever member; and a user-accessible member that applies a direct force to substrate 40, in a direction perpendicular to substrate 40, to move substrate 40 from one position to another. Likewise, housing 20 could take the form of a box (lower housing 22), with upper housing 24 serving as a lid thereto. Contacts 42 could be fixed to the upper housing, to contact a received stimulation lead 100 upon "closing" the upper housing with respect to the lower housing, or driven by actuator in a manner generally consistent with the preferred embodiment. For this modification, the alternative housing should provide access to an engaged stimulation lead so as to enable a user to better control stimulation lead direction and placement through use of a steering mechanism rather than manipulation of the stimulation lead and/or the connection assembly.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A connector to receive at least a portion of a stimulation lead adapted to accept a steering mechanism through a steering mechanism inlet, the connector comprising:

a housing having a receiving portion to receive at least a connector portion of such a stimulation lead; and at least one contact to electrically engage a connector portion of a stimulation lead received within the receiving portion, wherein the housing is adapted to provide access to a steering mechanism inlet of an engaged stimulation lead to enable selective insertion or withdrawal of a steering mechanism through such steering mechanism inlet, and wherein the housing is further adapted to operatively guide a distal end of a steering mechanism into a steering mechanism inlet of an engaged stimulation lead.

2. A connector in accordance with claim 1, further comprising a mechanism to selectively effect a translation of the at least one contact from the first position to the second position.

3. A connector in accordance with claim 1, wherein the at least one contact secures a connector portion of a stimulation lead within the receiving portion when the at least one contact is in the second position.

4. A connector in accordance with claim 1, further comprising a connecting element, coupled to the at least one contact, adapted for connection to an electrical energy source.

5. A connector to receive at least a portion of a stimulation lead adapted to accept a steering mechanism through a steering mechanism inlet, the connector comprising:

a housing having a reception channel to receive at least a connector portion of such a stimulation lead; and a plurality of contacts, movable from at least a first position to a second position, to engage a connector portion of a stimulation lead received within the reception channel when the at least one contact is at the second position, wherein the housing is adapted to provide access to a steering mechanism inlet of an engaged stimulation lead to enable selective insertion or withdrawal of a steering mechanism through such steering mechanism inlet.

6. A connector in accordance with claim 5, further comprising a mechanism to selectively effect a translation of at least one contact of the plurality of contacts from the first position to the second position.

7. A connector in accordance with claim 5, further comprising a connecting element, coupled to the plurality of contacts, adapted for connection to an electrical energy source.

8. A connector in accordance with claim 5, wherein the plurality of contacts secures a connector portion of a stimulation lead within the reception channel when the at least one contact is in the second position.

9. A connector to receive at least a portion of a stimulation lead adapted to accept a steering mechanism through a steering mechanism inlet, the connector comprising:

a connecting device to connect to an electrical energy source;

a housing having a reception space to receive at least a connector portion of a stimulation lead;

at least one contact, electrically coupled to the connecting device and further movable from at least a first position to a second position, to electrically engage a stimulation lead received within the reception space when the at least one contact is at the second position; and an actuator to effect a translation of the at least one contact from the first position to the second position, wherein the housing is adapted to provide access to a steering mechanism inlet of an engaged stimulation lead to enable selective insertion or withdrawal of a steering mechanism through such steering mechanism inlet.

* * * * *

UNITED STATES PATENT AND TRADEMARK OFFICE
CERTIFICATE OF CORRECTION

PATENT NO. : 6,154,678
DATED : November 28, 2000
INVENTOR(S) : B. Reno LAURO

It is certified that error appears in the above-identified patent and that said Letters Patent is hereby corrected as shown below:

Column 6, line 41 (claim 1, line 6), before "contact", insert --electrical--.

Column 6, line 52 (claim 1, line 17), before the period, insert --wherein the at least one electrical contact is adapted to translate from a first position, when the receiving portion receives a stimulation lead, to a second position, establishing an electrical connection with a connector portion of a stimulation lead--.

Column 7, line 3 (claim 5, line 6), before "contacts", insert --electrical--.

Signed and Sealed this

Twenty-fourth Day of April, 2001

Attest:

NICHOLAS P. GODICI

Attesting Officer    Acting Director of the United States Patent and Trademark Office